United States Patent [19]

Duch et al.

[11] Patent Number: 4,897,395

[45] Date of Patent: Jan. 30, 1990

[54] TREATMENT WITH DIALKOXY PYRIDOPYRIMIDINES

[75] Inventors: David S. Duch, Cary; Charles A. Nichol, Durham; Carl W. Sigel, Raleigh, all of N.C.

[73] Assignee: Burroughs Wellcome Co., Research Triangle Park, N.C.

[21] Appl. No.: 125,721

[22] Filed: Nov. 30, 1987

Related U.S. Application Data

[60] Continuation of Ser. No. 24,678, Mar. 11, 1987, abandoned, which is a continuation of Ser. No. 590,547, Mar. 19, 1984, Pat. No. 4,661,490, which is a continuation of Ser. No. 384,147, Jun. 1, 1982, abandoned, which is a division of Ser. No. 228,164, Jan. 23, 1981, Pat. No. 4,372,164, which is a continuation of Ser. No. 159,243, Jun. 13, 1980, abandoned.

[30] Foreign Application Priority Data

Jun. 14, 1979 [GB] United Kingdom ................. 7920703

[51] Int. Cl.$^4$ .......................................... A61K 31/505
[52] U.S. Cl. ..................................................... 514/258
[58] Field of Search ......................................... 514/258

[56] References Cited

U.S. PATENT DOCUMENTS 3,322,765  5/1967  Hitchings et al. .................. 514/258

FOREIGN PATENT DOCUMENTS 913710  12/1962  United Kingdom ................ 514/258
970583   9/1964  United Kingdom ................ 514/258
1084103  9/1967  United Kingdom ................ 514/258

Primary Examiner—Jerome D. Goldberg
Attorney, Agent, or Firm—Donald Brown

[57] ABSTRACT

Potent antiproliferative activity in combination with low inhibition of histamine N-methyltransferase has been found in a class of 2,4-diamino-6-(2,5-dialkoxybenzyl)-5-methylpyrido[2,3-d]pyrimidines.

5 Claims, No Drawings

TREATMENT WITH DIALKOXY PYRIDOPYRIMIDINES

PRIOR APPICATIONS

This application is a continuation of U.S. Ser. No. 024,678, filed Mar. 11, 1987 (now abandoned); which is a continuation of U.S. Ser. No. 590,547, filed Mar. 19, 1984 (now U.S. Pat. No. 4,661,490); which is a continuation of U.S. Ser. No. 384,147, filed June 1, 1982 (now abandoned); which is a division of U.S. Ser. No. 228,164, filed Jan. 23, 1981 (now U.S. Pat. No. 4,372,164); which is a continuation of U.S. Ser. No. 159,243, filed June 13, 1980 (now abandoned).

The present invention relates to 2,4-diaminopyrido(2,3-d)pyrimidines, to pharmaceutical formulations comprising such compounds and to their use in medicine.

U.K. patent No. 1 084 103 discloses 2,4-diaminopyrido(2,3-d)pyrimidines of the general formula (I):

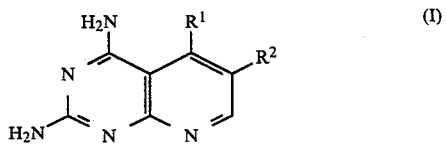

in which $R^1$ is an alkyl group and $R^2$ is an unsubstituted benzyl group or a benzyl group substituted by one or more halogen atoms, alkyl or alkoxy groups.

The compounds of formula (I) were described as having high in vitro and in vivo activity against bacteria or bacteria infections in experimental animals.

Subsequently it has been found that the compounds of formula (I) specifically disclosed in U.K. 1 084 103 show some inhibitory activity against mammalian dihydrofolate reductase (DHFR), and the activity was sufficient to render them potentially useful in the treatment of conditions where inhibition of mammalian DHFR is desirable. It has further been found that many of these compounds are potent inhibitors of histamine N-methyltransferase (HMT) an enzyme involved in the metabolism of histamine. In this manner they often cause an undesirable accumulation of histamine in organs and tissues. The effects of histamine as well known and any possibility of a further utility for these compounds was substantially diminished by their strong inhibition of HMT.

Further investigation showed that a number of other compounds of formula (I) also possess DHFR inhibitory activity but that these, too, were also potent inhibitors of HMT. Others, which had acceptably low levels of inhibition of HMT were found to have insufficient activity as inhibitors of DHFR.

It has now been surprisingly found that 2,4-diamino-6-(2,5-dimethoxybenzyl)-5-methylpyrido[2,3-d]pyrimidine, which is within the scope of formula (I) but not specifically disclosed in U.K. 1 084 103, is not only a very potent inhibitor of mammalian DHFR, but also has acceptably low inhibitory activity against HMT. This compound is represented by the formula (II) below and is useful in the treatment of proliferative diseases, such as psoriasis basal and squamous cell carbinomas of the skin, and various forms of cancer including leukemias, lymphomas, sarcomas and solid tumors.

The invention herein accordingly sets forth in antiproliferative properties of the compound of formula (II):

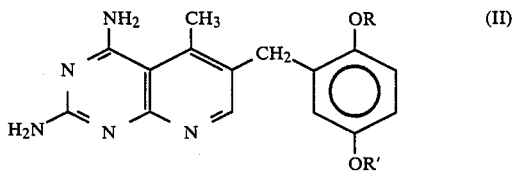

wherein R and R' are lower ($C_1$–$C_6$) alkyl and pharmaceutically acceptable acid addition salts thereof. Preferably mono-basic salts are provided. Preferably R and R' are methyl.

The compounds of formula (II) are their use in the treatment of infections caused by Streptococcus pyogenes and Streptococcus facalis were discovered earlier by another whose rights are assignable to Burroughs Wellcome Co.

The antiproliferative activity of the compound of formula (II) resides in the free base and thus the nature of the acid participating in the acid addition salts is of minor importance. Such acid addition salts include, for example, those derived from hydrochloric acid, hydroiodic acid, sulphuric acid, phosphoric acid, acetic acid, p-toluenesulfonic acid, methanesulfonic acid, maleic acid, lactic acid, citric acid, tartartic acid, succinic acid, oxalic acid, p-chlorobenzenesulphonic acid, isethinic acid, glucuronic acid, pahtothenic acid and lactobionic acid.

The compound of formula (II) may be prepared by any method known in the art for the preparation of compounds of analogous structure.

In particular the compound of formula (II) may be prepared by the reductive cleavage of the corresponding 7-substituted compounds of the formula (III):

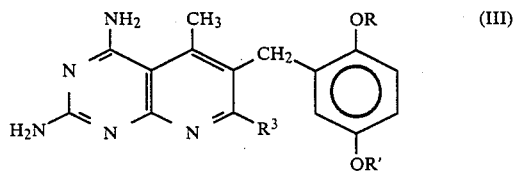

wherein R and R' are as defined above and $R^3$ is a leaving group capable of being removed by hydrogenolysis. Such groups include for example a mercapto or a halgeno (e.g. chloro) group.

Where the compound (III) $R^3$ is SH the dethiation may for instance be conveniently effected by reaction with a reducing agent, for example Raney nickel or Raney cobalt or by catalytic hydrogenation utilizing hydrogen in the presence of a catalyst such as palladium on charcoal.

The compound of formula (III) wherein $R^3$ is a mercapto group may be prepared from the corresponding 7-chloro compound (III) [$R^3$=Cl], by reaction with a hydrosulfide as described in U.K. patent No. 913 710 or by treatment of the corresponding 7-hydroxy compound with phosphorus pentasulfide.

In the case where $R^3$ is a halogen atom in the compound of formula (III) the compound of formula (II) may for instance be conveniently obtained by e.g. catalytic hydrogenation.

The compound of formula (II) may also be prepared by reacting 2,4,6-triaminopyrimidine (IV) with a compound of formula (V):

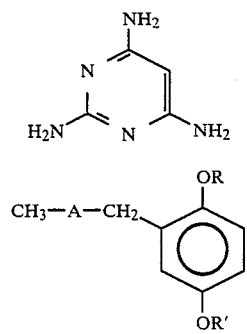

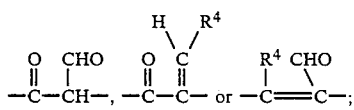

wherein A is selected from

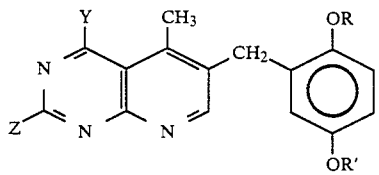

R and R' are as defined above; and $R^4$ is a leaving group such, for example, as a tertiary amino, alkoxy, alkylthio, halogeno, sulphonate or tosylate group.

The compounds of formula (II) may additionally be prepared by the conversion to amino groups, by methods known in themselves in pyrimidine chemistry, of the hydroxy and/or mercapto group(s) in the compound of formula (VI):

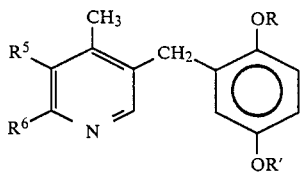

in which Y and Z are the same or different and are OH, SH or $NH_2$ provided that at least one of Y and Z is OH or SH.

Compounds of formula (VI) may be prepared by metods known in the art for the preparation of such compounds. In addition, those in which Y is OH or SH may be obtained for example by reaction of urea, guanidine or thiourea with a suitable compound of formula (VII):

in which R and R' are as defined above and $R^5$ is —$CO_2H$, $CO_2H$, $CO_2Alkyl$, $CONH_2$ or CN and $R^6$ is $NH_2$, Cl or Br.

While it is possible for a compound of formula (II) or an acid addition salt thereof (hereinafter referred to as the "active compounds") to be administered as the raw chemical it is preferably presented in the form of a pharmaceutical formulation.

The invention therefore further provides a pharmaceutical formulation comprising the active compound together with a pharmaceutically acceptable carrier therefore. The carrier must be "acceptable" in the sense of being compatible with the other ingredients of the formulation and not deleterious to the recipient thereof.

The invention additionally provides a method for the preparation of a pharmaceutical formulation comprising bringing into association an active compound and pharmaceutically acceptable carrier therefor.

Topical application is particularly suitable when the active compounds are for use in the treatment of proliferative skin diseases.

The term "topical" as applied herein relates to the use of the active ingredient incorporated in a suitable pharmaceutical carrier, and applied at the site of the disease for the exertion of local action.

Pharmaceutical formulations suitable for topical administration may be presented in anhydrous forms such as ointments, lotions, pastes, jellies, sprays, aerosols, and bath oils. The term ointment includes formulations (including creams) having oleaginous, absorption, water-soluble and emulsion type bases, for example petrolatum, lanolin, polyethylene glycols and mixtures thereof.

Topical formulations may contain a concentration of the active ingredient of from about 0.05 to about 2% w/w, preferably about 0.1 to about 1% w/w, most preferably about 0.2 to about 0.5% w/w.

Other pharmaceutical formulations include those suitable for oral, rectal, and parenteral administration although of those oral is preferred. The formulations may, where appropriate, be conveniently presented in discrete dosage units and may be prepared by any of the methods well known in the art of pharmacy. A convenient unit dose formulation contains the active compound in amount of from about 50 mg to about 1 g, preferably about 100 mg to about 500 mg, most preferably about 200 mg, to be taken once or several times daily.

All methods for the preparation of such formulations include the step of bringing into association the active compound with liquid carriers or finely divided solid carriers or both and then, if necessary shaping the product into the desired formulation.

Pharmaceutical formulations suitable for oral administration wherein the carrier is a solid are most preferably presented as unit dose formulations such as blouses, capsules, cachets or tablets each containing a predetermined amount of the active compound. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispensing agent. Molded tablets may be made by moulding an inert liquid diluent. Tablets may be optionally coated and, if uncoated, may be optionally scored. Capsules may be prepared by filling the active compound ingredients, into the capsule cases and then sealing them in the usual manner. Cachet are analogous to capsules wherein the active ingredient together with any accessory ingredient(s) are sealed in a rice paper envelope.

Pharmaceutical formulations suitable for oral administration wherein the carrier is a liquid may be presented as a solution or a suspension in an aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other material commonly used in the art, the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

As has been described above the compounds of the present invention are useful for the treatment of proliferative diseases. The inventon thus further provides a method for the treatment of a proliferative disease in mammals including humans which comprises the administration of an effective, non-toxic amount of compound of formula (II) or an acid addition salt thereof, once or several times a day orally, or applied topically.

The amount of compound of formula (II) required for therapeutic effect as an antiproliferative agent will of course vary not only with the particular salt used but also with the route of administration. In general, a suitable dose for the treatment of mammals (including humans) will lie in the range of from about 0.1 to about 100 mg per kilogram bodyweight (mg/kg) per day, preferably in the range from of about 2.0 to about 50 mg/kg, more preferably in the range of about 0.5 to about 20 mg/kg, not preferably in the range of about 1 to about 10 mg/kg.

Toxic manifestations attributable to the active compound are typically those associated with folate depletion, such as bone marrow depression, megaloblastic changes, and gastrointenstinal ulceration. Calcium leucovorin (calcium salt of 5-formyl-5,6,7,8-tetrahydrofolic acid) may be administered to effect reversal of these toxic manifestations or to prevent their occurrence. The administration of calcium leucovorin may be effected concurrently with treatment or at any stage therof whenever toxic symptoms appear.

Thus, the heamatological activity of the active compound can be prevented or reduced by the simultaneous administration of leucovorin. Consequently, tissue levels of the active compound may be safely raised by increasing the dose of the compound together with a simultaneous administration of leucovorin.

The following Examples, which illustrate the invention, should in no way be construed as constituting a limitation thereof.

EXAMPLE 1

2,4-Diamino-5-methyl-6-(2,5-dimethoxybenzyl)-pyrido[2,3-]pyrimidine

A mixture of 2,5-dimethoxybenzaldehyde (100 g), ethyl acetoacetate (84.5 g) and anhydrous benzene (200 ml), piperidine (6 ml) andd acetic acid (12 ml) was heated at reflux for 3 hours in an apparatus fitted with a Dean-Stark trap to collect the azeotropically distilled water. The reaction mixture was cooled, benzene (300 ml) added, and the solution was washed successively with water (100 ml), cold 0.1N hydrochloric acid (200 ml), 5% aqueous sodium bicarbonate (200 ml) and dilute acetic acid (100 ml) and dried over anhydrous magnesium sulfate. The solvent was then removed under reduced pressure and the residual oil distilled, b.p. 169°–170° C./0.3 mm Hg. The product, ethyl α-(2,5-dimethoxybenzylidene)acetoacetate, solidified on standing (104 g, m.p. 68°–69° C.) and was recrystallized from ethanol-pentane (m.p. 72°–73° C.). A portion (38 g) of the product was reduced catalytically in the presence of palladium on charcoal catalyst (Pd/C) in ethyl acetate (150 ml). The product, after removal of solvent, was purified by distillation under reduced pressure to give ethyl α-(2,5-dimethoxybenzyl)acetoacetate, b.p. 146°–148° C./0.3 mm Hg.

A mixture of ethyl α-(2,5-dimethoxybenzyl)acetoacetate (21.2 g), 2,4,6-triaminopyrimidine (10 g) and diphenyl ether (100 ml) was heated at 190°–230° C. for 15 hours in an apparatus fitted with a Dean-Stark trap and water-ethanol (4 ml) was collected. Methanol (200 ml) and ethanol (50 ml) were added to the cooled reaction mixture. The resulting solid was collected by filtration and treated with boiling water (1 l) to give 2,4-dianimo-5-methyl-6-(2,5-dimethoxybenzyl)-7-oxo-7,8-dihydropyrido[2,3-d]pyrimidine (17 g), m.p. 325°–326° C.

2,4-Diamino-5-methyl-6-(2,5-dimethoxybenzyl)-7-oxo-7,8-dihydropyrido[2,3-d]pyrimidine (8 g) was chlorinated by treatment with Vilsmeier reagent prepared by slowly adding thionyl chloride (28.6 ml) in dry chloroform (25 ml) to a solution of dimethylformamide (17.5 ml) in chloroform (100 ml) at 0°–5° C.

The cold mixture of the pyridopyrimidine and Vilsmeier reagent was stirred, gradually allowed to reach ambient temperature and then heated at a reflux for 3 hours. It was then treated with ethanolic base (80 ml) maintaining the temperature at 25°–30° C. with cooling. The brown product formed was isolated, treated further with aqueous ammonia and then recrytallized from ethanol to give 2,4-diamino-5-methyl-6-(2,5-dimethoxybenzyl)-7-chloro-pyrido[2,3-d]pyrimidine, m.p. 193°–196° (dec.).

The chloro compound (0.3 g) was dissolved in ethanol (200 ml) containing potassium hydroxide (0.2 g). Palladium on charcoal catalyst (0.2 g) was added and hydrogenation commenced. Reduction was complete after 48 hours and yielded 2,4-diamino-5-methyl-6-(2,5-dimethoxybenzyl)pyrido[2,3-d]pyrimidine, m.p. 252°–254° C.

EXAMPLE 2

Inhibition of Mammalian Dihydrofolate Reductase (DHFR) by 2,4-Diamino-5-methyl-6-benzylpyrido(2,3-d)pyrimidines The inhibitory effect of the test compounds against DHFR partially purified from rat liver was determined. The results are given in Table 1 below. An $IC_{50}$ of $5 \times 10^{-8}M$ or less is considered significant potency, an $IC_{50}$ of $1 \times 10^{-8}M$ or less being particularly significant potency.

TABLE 1

TEST COMPOUND

[Structure: 2,4-diamino pyrido(2,3-d)pyrimidine core with $R^1$ at 5-position and $R^2$ at 6-position]

| $R^1$ | $R^2$ | $IC_{50} \times 10^{-8}$ M |
|---|---|---|
| $CH_3$ | $-CH_2-C_6H_5$ | 4 |
| $CH_3$ | $-CH_2-(2\text{-}Cl\text{-}C_6H_4)$ | 1.6 |
| $CH_3$ | $-CH_2-(4\text{-}CH_3\text{-}C_6H_4)$ | 2.7 |
| $CH_3$ | $-CH_2-(3\text{-}OCH_3\text{-}C_6H_4)$ | 5.0 |
| $CH_3$ | $-CH_2-(4\text{-}OCH_3\text{-}C_6H_4)$ | 5.3 |
| $CH_3$ | $-CH_2-(4\text{-}C_2H_5\text{-}C_6H_4)$ | 9 |
| H | $-CH_2-C_6H_5$ | 25 |
| $CH_3$ | $-CH_2-(2,4\text{-}(OCH_3)_2\text{-}C_6H_3)$ | 0.15 |

EXAMPLE 3

Inhbition of Histamine N-Methyltransferase (HMT) by 2,4-Diamino-5-methyl-6-benzylpyrido(2,3-d)pyrimidines The effect of the test compounds used in Example 3 against HMT was determined. The results are given in Table 2. An inhibition of less than 20% was considered acceptable and the lack of any effect on this enzyme is most desirable since any interference with histamine metabolism should be minimized.

TABLE 2

TEST COMPOUND

[Structure: 2,4-diamino pyrido(2,3-d)pyrimidine core with $R^1$ at 5-position and $R^2$ at 6-position]

| $R^1$ | $R^2$ | % Inhibition of HMT at $10^{-5}$ M |
|---|---|---|
| $CH_3$ | $-CH_2-C_6H_5$ | 51 |
| $CH_3$ | $-CH_2-(2\text{-}Cl\text{-}C_6H_4)$ | 59 |
| $CH_3$ | $-CH_2-(2\text{-}OCH_3\text{-}C_6H_4)$ | 18 |
| $CH_3$ | $-CH_2-(4\text{-}OCH_3\text{-}C_6H_4)$ | 20 |
| $CH_3$ | $-CH_2-(4\text{-}C_2H_5\text{-}C_6H_4)$ | 55 |
| H | $-CH_2-C_6H_5$ | 48 |
| $CH_3$ | $-CH_2-(2,5\text{-}(OCH_3)_2\text{-}C_6H_3)$ | 11 |

EXAMPLE 4

Antitumor Effect of 2,4-Diamino-6-(2,5-dimethoxybenzyl)-5-methylpyrido(2,3-d)pyrimidine Against a Solid Tumor (Carcinoma)

Solid Walker 256 tumors were implanted subcutaneously into three groups of rats. On the third day after implantation with the tumors, drug treatment was commenced and continued for 5 successive days. One group of rats was treated with 2,4-diamino-6-(2,5-dimethoxyphenyl)-5-methylpyrido[2,3-d]pyrimidine at a dose of 25 mg/kg q.i.d., a second group was treated with the same compound at 15 mg/kg b.i.d.; the third group was left untreated as controls. After 17 days the treated groups of rats showed mean tumor volumes of 29% and 10% respectively of the untreated group.

In a second study tumors were implanted subcutaneously and drug treatment delayed until 10 days after implantation. Drug treatment consisted of 30 mg/kg q.i.d. on days 10-13 and 50 mg/kg on days 20, 24 and 28 after tumor implantation. Mean tumor volumes were measured during the course of this study. Tumor volumes in animals which received no treatment increased rapidly whereas those in animals which receive drug treatment showed a decrease in mean tumor volume during the period of observation. Twenty-three days after tumor implantation the T/C was 0.03.

EXAMPLE 5

Antileukemic Effect of 2,4-Diamino-6-(2,5-dimethoxybenzyl)-5-methyl-pyrido(2,3-d)pyrimidine Leukemia P388 cells were inoculated intraperitoneally in CDF, Charles River female mice, each animal receiving $10^6$ cells. On the second day after implantation with the leukemia cells, drug treatment was commenced and continued twice daily for three days. Four groups of mice were treated with 2,4-diamino-6-(2,5-dimethoxybenzyl)-5-methylpyrido(2,3-d)pyrimidine at doses of 22, 33.5, 50 and 75 mg/kg of body weight and a fifth group was left untreated as a control. All of the untreated mice died from the leukemia between the 10th and 12th day with a median survival of 11 days. All of the treated mice survived for periods longer than the untreated animals with a % increase in life span of 145%, 159% 140% and 154% for the drug treated grous receiving 22, 33.5, 50 and 75 mg/kg doses, respectively. This is a highly significant effect and there was no evidence of drug-related toxicity.

Within the same experiment, two closely related compounds were tested for antileukemic activity at the same dosage levels of 22, 33.5, 50 and 75 mg/kg, respectively, and the same schedule of treatment. The corresponding pyridopyrimidine with a 6-(4-methoxybenzyl) substituent was inactive at all doses and the 6-(2-chlorobenzyl) compound had only marginal or slight activity. Thus, the 6-(2,5-dimethoxybenzyl) compound has substantially greater antileukemic activity than these compounds of similar structure.

EXAMPLE 6

Water Soluble Ointments

|  | Amount (g) |
|---|---|
| 2,4-Diamino-5-methyl-6-(2,5-dimethoxybenzyl)pyrido[2,3-d]pyrimidine | 0.5 |
| Polyethylene glycol 300 | 20.0 |
| Polyethylene glycol 1500 | 79.5 |
| Total | 100.0 |

EXAMPLE 7

Skin Cream

|  | Amount (g) |
|---|---|
| 2,4-Diamino-5-methyl-6-(2,5-)dimethoxybenzyl)pyrido[2,3-d]pyrimidine | 0.5 |
| Glyceryl monostearate | 20.0 |

-continued

|  | Amount (g) |
|---|---|
| Methylparaben | 0.3 |
| Petrolatum, light liquid | 4.0 |
| Propylene glycol | 5.0 |
| Span 60 | 2.0 |
| Tween 61 | 4.0 |
| Water | 64.2 |
| Total | 100.0 |

EXAMPLE 8

Injectable

|  | Amount |
|---|---|
| 2,4-Diamino-5-methyl-6-(2,5-dimethoxybenzyl)pyrido[2,3-d]pyrimidine | qs to 5 mg/ml |
| Propylene glycol | 40 ml |
| Ethanol | 11 ml |
| Water | 49 ml |

EXAMPLE 9

Injectable

|  | Amount |
|---|---|
| 2,4-Diamino-5-methyl-6-(2,5-dimethoxybenzyl)pyrido[2,3-d]pyrimidine | qs to 5 mg/ml |
| Propylene glycol | 40 ml |
| 5% Dextrose solution | 60 ml |

We claim:

1. The method of decreasing the volumn of a carcinoma in a human suffering from said carcinoma comprising administering to said human an effective carcinoma-volumn decreasing amount of the compound 2,4-diamino-6-(2,5-dimethoxybenzyl)-5-methyl-pyridopyrimidine or a pharmaceutically acceptable salt thereof.

2. The method of treating carcinoma in a human suffering from a carcinoma comprising the administration to said human of an effective anticarcinoma treatment amount of 2,4-diamino-6-(2,5-dimethoxybenyl)-5-methylpyridopyrimidine or a pharmaceutically acceptable salt thereof.

3. The method of treatoing sarcoma in a human suffering from a sarcoma which comprises administering to said human an effective antisarcoma amount of 2,4-diamino-6-(2,5-dimethoxybenzyl)-5-methyl-pyridopyrimidine or a pharmaceutically acceptable salt thereof.

4. The method of treating lymphoma in a human suffering from a lymphoma which comprises administering to said human an effective anti-lymphoma amount of 2,4-diamino-6-(2,5-dimethoxybenzyl)-5-methylpyridopyrimidine or a pharmaceutically acceptable salt thereof.

5. The method of treating leukemia in a human suffering from leukemia which comprises administering to said human an effective antileukemia amount of 2,4-diamino-6-(2,5-dimethoxybenzyl)-5-methyl-pyridopyrimidine or a pharmaceucically acceptable salt thereof.

* * * * *

UNITED STATES PATENT AND TRADEMARK OFFICE
CERTIFICATE OF CORRECTION

PATENT NO. : 4,897,395

DATED : January 30, 1990

INVENTOR(S) : David S. Duch, Charles A. Nichol & Carl W. Sigel

It is certified that error appears in the above-identified patent and that said Letters Patent is hereby corrected as shown below:

On the cover page:

[60] Under: RELATED U.S. APPLICATION DATA

Line 6, Pat. No. 4,372,164, should be Pat. No. 4,372,957.

Signed and Sealed this

Ninth Day of July, 1991

Attest:

HARRY F. MANBECK, JR.

Attesting Officer

Commissioner of Patents and Trademarks